United States Patent
Kuhnle et al.

(10) Patent No.: US 6,720,462 B2
(45) Date of Patent: Apr. 13, 2004

(54) METHOD FOR PRODUCING AROMATIC ALCOHOLS, ESPECIALLY PHENOL

(75) Inventors: Adolf Kuhnle, Marl (DE); Mark Duda, Ludwigshafen (DE); Uwe Tanger, Bochum (DE); Roger Arthur Sheldon, VA Rijswijk (NL); Sasidharan Manickam, Tamil Nadu (IN); Isabella W. C. E. Arends, SL's Gravenhage (NL)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/239,185

(22) PCT Filed: Mar. 22, 2001

(86) PCT No.: PCT/EP01/03288

§ 371 (c)(1),
(2), (4) Date: Sep. 26, 2002

(87) PCT Pub. No.: WO01/74767

PCT Pub. Date: Oct. 11, 2001

(65) Prior Publication Data

US 2003/0083527 A1 May 1, 2003

(30) Foreign Application Priority Data

Mar. 30, 2000 (DE) ......................................... 100 15 874

(51) Int. Cl.[7] .............................................. C07C 37/08
(52) U.S. Cl. ..................................... 568/768; 568/573
(58) Field of Search ................................ 568/768, 573

(56) References Cited

U.S. PATENT DOCUMENTS

| | | | |
|---|---|---|---|
| 4,293,719 A | * | 10/1981 | Velenyi |
| 4,299,991 A | * | 11/1981 | Velenyi |
| 4,487,970 A | * | 12/1984 | Drake |
| 5,030,739 A | | 7/1991 | Foricher et al. |
| 6,023,000 A | | 2/2000 | Fritz-Langhals et al. |
| 6,291,718 B1 | * | 9/2001 | Matsui |

FOREIGN PATENT DOCUMENTS

| | | |
|---|---|---|
| DE | 197 23 890 | 12/1998 |
| EP | 0 198 351 | 10/1986 |
| EP | 0858 835 | 8/1998 |
| EP | 0 864 555 | 9/1998 |
| EP | 0 878 234 | 11/1998 |
| EP | 0 878 458 | 11/1998 |
| EP | 0 927 717 | 7/1999 |

OTHER PUBLICATIONS

"Kirk–Othmer Encyclopedia of Chemical Technology", 4th Ed., vol. 18, pp. 593–598.*

Y. Ishii, Journal of Molecular Catalysis A: Chemical, vol. 117, pp. 123–137, A Novel Catalysis of N–Hydroxyphthalimide (NHPI) Combined with Co(acac)$_n$ ( n=2 or 3) in the Oxidation of Organic Substrates with Molecular Oxygen, 1997.

Y. Ishii, et al., J. Org. Chem. vol. 60, No. 13, pp. 3934–3935, "A Novel Catalysis of N–Hydroxyphthalimide in the Oxidation of Organic Substrates by Molecular Oxygen", 1995.

K. Matsunaka, et al., Tetrahedron Letters, vol. 40, pp. 2165–2168, "A Remarkable Effect of Quaternary Ammonium Bromide for the N–Hydroxyphthalimide–Catalyzed Aerobic Oxidation of Hydrocarbons", 1999.

T. Iwahama, et al., Chem. Comm., pp. 727–728, Epoxidation of Alkenes Using Dioxygen in the Presence of an Alcohol Catalyzed by N–Hydroxyphthalimide and Hexafluoroacetone without any Metal Catalyst, 1999.

C. Einhorn, et al., Chem. Commun., pp. 447–448, "Oxidation of Organic Substrates by Molecular Oxygen Mediated by N–Hydroxyphthalimide (NHPI) and Acetaldehyde", 1997.

M. L. Farberov, et al., English Abstracts of Neftekhimiya, vol. 9, No. 1, pp. 107–115, "Simultaneous Preparation of Phenol and Cyclohexanone by the Oxidation of Phenylcyclohexane", 1969.

* cited by examiner

Primary Examiner—Michael L. Shippen
(74) Attorney, Agent, or Firm—Oblon, Spivak, McClelland, Maier & Neustadt, P.C.

(57) ABSTRACT

The invention relates to a process for preparing phenol derivatives by catalytic oxidation of an aromatic hydrocarbon to the hydroperoxide and subsequent cleavage of the hydroperoxide to give the phenol derivative and a ketone, wherein a compound of the formula I

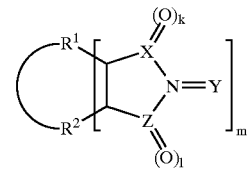

where $R^1$, $R^2$=H, aliphatic or aromatic alkoxy radical, carboxyl radical, alkoxycarbonyl radical or hydrocarbon radical, in each case having from 1 to 20 carbon atoms, $SO_3H$, $NH_2$, OH, F, Cl, Br, I and/or $NO_2$, where $R^1$ and $R^2$ are identical or different radicals or $R^1$ and $R^2$ may be joined to one another via a covalent bond, and

X, Z=C, S, $CH_2$

Y=O, OH k=0, 1, 2 l=0, 1, 2 m=1–3;

is used as oxidation catalyst in the presence of a free-radical initiator, where the molar ratio of the catalyst to the aromatic hydrocarbon is less than 10 mol %.

18 Claims, No Drawings

METHOD FOR PRODUCING AROMATIC ALCOHOLS, ESPECIALLY PHENOL

The invention relates to a process for preparing aromatic alcohols, in particular phenol, by catalytic oxidation of aromatic hydrocarbons to the corresponding hydroperoxides and subsequent cleavage of the hydroperoxides.

To obtain hydroxyl-containing aromatic compounds such as phenol, it is not possible to convert benzenes directly in one stage and in high yields into the phenols by selective oxidation using atmospheric oxygen. Either the aromatic ring is not attacked at all or the oxidation continues to carbon dioxide since the aromatic ring which has been functionalized by oxygen atoms is more reactive than the starting benzene.

For this reason, the hydroxyl group has to be introduced into the aromatic system via intermediates.

The cumene process is frequently employed for preparing phenol derivatives from benzene derivatives, i.e. aromatic hydrocarbons. In this process, for example, cumene prepared from benzene and propene by alkylation is peroxidized and the oxidation product is then cleaved into the two products of value phenol and acetone ("Hock process"). Owing to its good economics, this process has become established worldwide for the production of phenol.

Both the preparation of the starting material prepared by alkylation, e.g. cumene, cyclohexylbenzene (in the Hock process, cyclohexylbenzene gives not acetone but cyclohexanone) and cyclododecylbenzene (in the Hock process, cyclododecylbenzene gives cyclododecanone), and the acid-catalysed cleavage and rearrangement to phenol which follow the oxidation step generally proceed with high selectivity to give high yields.

The economics of the Hock process are therefore particularly critically dependent on the selectivity of the oxidation of the tertiary carbon atom and on the reaction rate and the conversion.

For this reason, a great deal of effort has been directed, in particular, at the preparation of the peroxide. In practice, the oxidation of the starting material by means of atmospheric oxygen has proven useful. Additives such as free-radical initiators or the use of other oxidants, e.g. the compounds $KMnO_4$, $CrO_3$ and $HNO_3$ frequently used for the oxidation of hydrocarbons, adversely affect the selectivity, lead to disposal problems, produce ecologically unacceptable by-products and corrode the plant.

The use of metal redox catalysts makes it possible to utilize molecular oxygen for the oxidation of organic compounds. A series of industrial processes are based on the metal-catalysed autooxidation of hydrocarbons. Thus, for example, the oxidation of cyclohexane to cyclohexanol or cyclohexanone by means of $O_2$ is carried out using cobalt salts. This process is based on a free-radical chain mechanism. The diradical oxygen reacts with a hydrocarbon radical to form a peroxy radical and subsequent chain propagation by abstraction of an H atom from a further hydrocarbon. Apart from metal salts, it is also possible for organic molecules to function as free-radical initiators.

A disadvantage of this process is that the selectivity drops very severely with increasing conversion and the process therefore has to be operated at a low conversion level. Thus, for example, the oxidation of cyclohexane to cyclohexanol/cyclohexanone is carried out at a conversion of from 10 to 12% so that the selectivity is from 80 to 85% ("Industrielle Organische Chemie" 1994, 261, VCH Verlagsgesellschaft mbH, D-69451 Weinheim). In a further important industrial autooxidation process for cumene oxidation, the conversion is about 30% as a cumene hydroperoxide sensitivity of about 90% (loc. cit. p. 495 ff).

An alternative to metal salt catalysts is provided by the use of catalyst systems or mediator systems such as N-hydroxyphthalimide (NHPI). However, the reaction rate in the processes described in the literature is not satisfactory despite the high amount of mediator (up to an equimolar amount based on the substrate) (J. Mol. Catalysis A. 1997, 117, 123–137). Thus, U.S. Pat. No. 5,030,739 describes the use of N-hydroxydicarboximides for the oxidation of isoprene derivatives to the corresponding acrolein compounds. Combined oxidation/dehydration of cyclohexadienes or six-membered ring systems such as α-terpenes leads to the cumene derivative which is, however, not oxidized further. This process is therefore unsuitable for the conversion of cumene into cumene hydroperoxide.

In general, amounts of mediator of at least 10 mol % based on the substrate are used, with larger amounts of mediator being used to increase the reaction rate (J. Org. Chem. 1995, 60, 3934–3935). The product selectivity is not satisfactory for industrial use. Thus, oxidation of cumene using NHPI gives a product mixture comprising acetophenone as main product, but the desired oxidation product cumene hydroperoxide was not able to be isolated (J. Org. Chem. 1995, 60, 3934–3935).

A further development of the system is the use of cocatalysts. Cocatalysts which can be used are metal compounds, in particular heavy metal salts, enzymes or strong Brönsted acids. Thus, Ishii et al., demonstrated that NHPI in combination with metal salts as cocatalyst can display advantages over the oxidation using NHPI without cocatalyst (e.g. EP 0878234, EP 0864555, EP 0878458, EP 0858835, JP 11180913, J. Mol. Catalysis A. 1997, 117, 123–137). However, a disadvantage of these systems is, apart from the undesirable heavy metal content, the large amount of NHPI used here, too. To ensure a satisfactory reaction rate, at least 10 mol % of mediator has to be used. A further disadvantage is that some of the redox metals used catalysed further reactions of the products and thus reduce the selectivity of the reaction.

Processes which use only a mediator without a cocatalyst have also become known. However, these are restricted to the oxidation of particularly activated substrates such as ethers, esters or isoprene derivatives.

Thus, the oxidation of cumene using the system NHPI/cobalt acetate gives a product mixture comprising acetophenone (selectivity: 54%), 2-phenyl-2-propanol (10%) and phenol (17%) (J. Mol. Catal. A 1997, 117, 123–137). The desired product cumene hydroperoxide is formed only as an intermediate and is not stable under the prevailing process conditions. The phenol wanted as final product is obtained in relatively minor amounts compared to the primary oxidation product acetophenone.

A further process variant comprises the use of NHPI in combination with alcohols or aldehydes (Chem. Commun, 1999, 727–728, Tetrahedron Letters 1999, 40, 2165–2168, Chem. Commun. 1997, 447–448). Disadvantages of these processes are the formation of coproducts and the high mediator/substrate ratio employed (10 mol %). DE 19723890 describes an oxidation system comprising an organic mediator and the redox enzyme laccase for the preparation of aromatic and heteroaromatic aldehydes and ketones. Here too, the amount of mediator used is very high. In addition, due to the use of an enzyme, this process involves a complicated reaction system with a biologically necessary buffer system which restricts broad applicability of the system.

It is an object of the present invention to develop a heavy-metal-free or metal-free process for preparing aromatic alcohols, in particular phenols, by catalytic oxidation of hydrocarbons to the hydroperoxides with subsequent cleavage of the hydroperoxides, which process displays high selectivities at high conversions.

It has surprisingly been found that compounds of the type

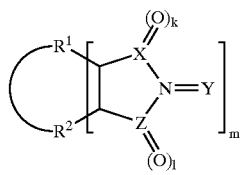

I can be used even without heavy metals or strong acids as cocatalysts for the oxidation of aromatic hydrocarbons to the corresponding hydroperoxides.

The present invention accordingly provides a process for preparing phenol derivatives by catalytic oxidation of an aromatic hydrocarbon to the hydroperoxide and subsequent cleavage of the hydroperoxide to give the phenol derivative and a ketone, wherein a compound of the formula I

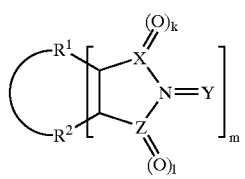

I where $R^1$, $R^2$=H, aliphatic or aromatic alkoxy radical, carboxyl radical, alkoxycarbonyl radical or hydrocarbon radical, in each case having from 1 to 20 carbon atoms, $SO_3H$, $NH_2$, OH, F, Cl, Br, I and/or $NO_2$, where $R^1$ and $R^2$ are identical or different radicals or $R^1$ and $R^2$ may be joined to one another via a covalent bond, and

X, Z=C, S, $CH_2$

Y=O, OH k=0, 1, 2 l=0, 1, 2 m=1–3;

is used as oxidation catalyst in the presence of a free-radical initiator, where the molar ratio of the oxidation catalyst to the aromatic hydrocarbon is less than 10 mol %.

Examples of oxidation catalysts of the formula I are N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2dicarboximide, N-hydroxynaphthalimide sodium salt or N-hydroxy-o-benzenedisulphonimide.

In the process of the invention, no metal compounds or enzymes are used as cocatalyst. The process is preferably carried out in organic solvents in the absence of strong acids, although the use of an aqueous solution whose pH is in the weakly acid to basic region is likewise possible.

The molar ratio of the oxidation catalyst to the aromatic hydrocarbons can be from $10^{-6}$ mol % to 10 mol %, preferably from $10^{-6}$ to 5 mol %, very particularly preferably from $10^{-6}$ to 2.5 mol % and in a specific embodiment in the range from $10^{-6}$ to 1 mol %.

The use of the oxidation catalyst (mediator) of the formula I in this small ratio to the aromatic hydrocarbon to be oxidized surprisingly results not only in high conversions after short reaction times but also in a high selectivity compared with the prior art. A further advantage of the process of the invention is the improvement in the economics caused by the reduction in the amount of mediator.

The process of the invention can be carried out in a manner similar to the Hock process for preparing phenol, as described in "Industrielle Organische Chemie" 1994, 383 ff, VCH Weinheim, and can be broken down into the individual steps oxidation of the aromatic hydrocarbon to the hydroperoxide isolation of the hydroperoxide cleavage of the hydroperoxide to give the desired phenol derivative and a ketone separate isolation of the phenol derivative and the ketone, in accordance with the following reaction scheme:

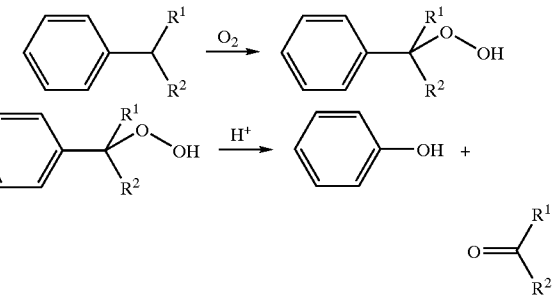

$R^1$ and $R^2$ can, for example, be as defined for the formula IV. The Hock process is used industrially for preparing phenol from cumene, i.e. $R^1=R^2=CH_3$.

The cleavage of the hydroperoxide can be carried out with the aid of a catalytic amount of a mineral acid, e.g. $H_2SO_4$, or a solid acid, e.g. a zeolite.

In specific embodiments of the process of the invention, it is also possible to use derivatives or specific cases of compounds of the formula I. These are hereinafter designated by the formulae II and III.

Preference is given to mediators or oxidation catalysts of the formula II, i.e. compounds of the formula I in which m=1. The meanings of $R^1$, $R^2$, X, Y, Z, k, l are as in formula I.

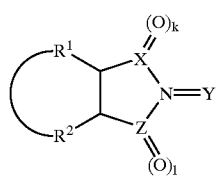

II

Particular preference is given to mediators or oxidation catalysts of the formula III

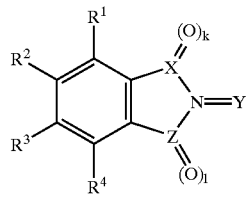

III where

R$^1$, R$^2$, R$^3$, R$^4$=H, aliphatic or aromatic alkoxy radical, carboxyl radical, alkoxycarbonyl radical or hydrocarbon radical, in each case having from 1 to 20 carbon atoms, SO$_3$H, NH$_2$, OH, F, Cl, Br, I and/or NO$_2$, where R$^1$, R$^2$, R$^3$ and R$^4$ may be identical or different radicals, and

X, Z=C, S, CH$_2$

Y=O, OH k=0, 1, 2 l=0, 1, 2.

In a particular embodiment of the invention, the oxidation of the aromatic hydrocarbon to the hydroperoxide is carried out in the gas phase or in the liquid phase, e.g. in each case at a temperature of from 0 to 500° C., preferably at a temperature of from 50 to 300° C. and particularly preferably from 50 to 200° C. It is possible to use either a solvent or solvent mixture or the aromatic hydrocarbon itself as solvent.

The substrates to be oxidized are aromatic hydrocarbons. These can be substituted or unsubstituted. The process of the invention enables many of these compounds to be oxidized selectively to the hydroperoxide and subsequently reacted further to give the phenol derivative.

In principle, all aromatic hydrocarbons having a primary, secondary or tertiary carbon atom can be oxidized by means of the process of the invention to form the corresponding hydroperoxide, but preference is given to using aromatic hydrocarbons having a secondary or tertiary carbon atom, particularly preferably compounds which have a tertiary carbon atom and have the formula IV

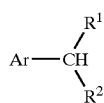

IV where

R$^1$, R$^2$=aliphatic hydrocarbon radical having from 1 to 20 carbon atoms, where R$^1$ and R$^2$ are identical or different radicals and R$^1$ and R$^2$ are joined to one another via a covalent bond and Ar=aromatic hydrocarbon radical.

Examples of compounds of the formula IV are cumene, cyclohexylbenzene, cyclododecylbenzene, ethylbenzene and 2-n-butylbenzene.

Further, preferred substrates for the process of the invention are compounds of the formulae V, VI, VII, VIII and IX, where Ar is an aromatic hydrocarbon radical such as a phenyl radical (C$_6$H$_5$—)

V

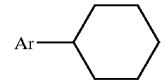

VI

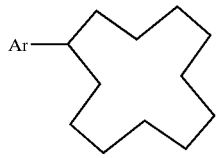

VII

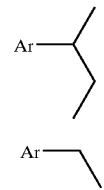

VIII

IX

The reaction mixture contains a free-radical initiator which decomposes to form free radicals, i.e. the free-radical-initiating moieties, for example a peroxy compound or an azo compound.

Examples of such compounds are cumene hydroperoxide, cyclohexylbenzene hydroperoxide, cyclododecylbenzene hydroperoxide, 1,4-di(2-neodecanoyl-peroxyisopropyl)benzene, acetylcyclohexanesulphonyl peroxide, cumyl peroxyneodecanoate, dicyclohexyl peroxydicarbonate, di(4-tert-butylcyclohexyl) peroxydicarbonate, di(2-ethylhexyl) peroxydicarbonate, dimyristyl peroxydicarbonate, dicetyl peroxydicarbonate, tert-butyl peroxyneodecanoate, tert-amyl peroxyneodecanoate, tert-amyl peroxypivalate, tert-butyl peroxypivalate, diisononanoyl peroxide, didecanoyl peroxide, tert-butyl peroxy-2-ethylhexanoate, tert-butyl peroxyisononanoate, 2,2'-di-tert-butylperoxybutane, di-tert-butyl peroxybenzoate, di-tert-butyl peroxide, tert-butyl hydroperoxide, 3,4-dimethyl-3,4-diphenylhexane, dibenzoyl peroxide, 1,4-di-tert-butylperoxycyclohexane, tert-butyl peroxy(ethylhexyl) carbonate, 1,1-di-tert-butylperoxycyclohexane, 2,2'-azobis(2,4-dimethylvaleronitrile), 2,2'-azobis(2-methylpropionitrile), 1,1'-azobis(cyclohexanecarbonitrile) or cyclohexyl hydroperoxide. Of course, it is also possible to use peroxides and azo compounds formed as intermediates as free-radical initiators.

Preference is given to a free-radical initiator which contains an oxygen atom bound to a primary, secondary or tertiary carbon atom, particularly preferably a free-radical initiator which is derived from the end product and contains at least one oxygen atom bound to a primary, secondary or tertiary carbon atom. The free-radical initiator is either added separately or is, as mentioned above, generated as an intermediate during the reaction or is even, since the plant cannot be made absolutely clean, present in small amounts from previous reactions. Examples of such compounds are cumene hydroperoxide (1-methyl-1-phenylethyl hydroperoxide), cyclohexylbenzene hydroperoxide (1-phenylcyclohexyl hydroperoxide), cyclododecylbenzene hydroperoxide (1-phenylcyclododecyl hydroperoxide) and 2-n-butylbenzene hydroperoxide (1-methyl-1-phenylpropyl hydroperoxide).

In the process of the invention, the concentration of the free-radical-initiating moiety (e.g. hydroxy radical) at the beginning of the reaction is frequently lower than the concentration of the catalyst. However, it needs to be ensured that intermediate formation of these compounds occurs during the course of the reaction, so that the concentration of the free-radical-initiating moieties increases during the course of the reaction.

The oxidation product formed can be isolated as such, but direct further reaction of this compound to give a further product, e.g. the desired phenol derivative, is also possible. Isolation of the product can be carried out by any customary industrial method, e.g. distillation.

The process of the invention can be carried out either batchwise, in a fed batch (feed stream process) or continuously.

The process of the invention can be carried out using an oxygen-containing gas as oxidant. The proportion of oxygen in the gas can be from 5 to 100% by volume. Preference is given to using atmospheric oxygen or pure oxygen as oxidant. In any case, intimate mixing of the liquid phase and the gaseous phase has to be ensured. This can be achieved, for example, in stirred vessels by means of an appropriate stirrer speed or by means of internals and in tube reactors by means of packing or by use of bubble columns.

However, it is also possible to produce the product in a type of reactive column. The catalyst system would then be arranged centrally in such a way that mixing with hydroperoxide formed in the liquid phase is not possible. This can be achieved, for example, by means of membranes having an appropriate pore size. Unreacted cumene would be separated off at the top.

The process of the invention can be carried out either under slightly subatmospheric pressure or under atmospheric pressure (1 bar) or under superatmospheric pressure up to 100 bar. Preference is given to a pressure of from 1 bar to 50 bar; particular preference is given to a pressure of from 1 bar to 20 bar.

The following examples illustrate the invention without restricting its scope.

The conversion in the oxidation was determined firstly by titration of the peroxide with iodine and secondly by GC analysis using an internal standard (naphthalene). The selectivity of the oxidation reaction was likewise determined by GC analysis using an internal standard (likewise naphthalene). The conversion and the selectivity of the cleavage reaction were determined by GC analysis using an internal standard (naphthalene). The selectivity to the cleavage products is always based on the starting material to be oxidized.

EXAMPLE 1a (ACCORDING TO THE INVENTION)

In a round-bottom flask fitted with superposed reflux condenser, 30 mmol of cumene are admixed at a temperature of 125° C. with 0.3 mmol of N-hydroxyphthalimide and 0.6 mmol of cumene hydroperoxide. The reaction mixture is stirred at the specified temperature under an oxygen atmosphere of 1 bar for 8 hours. Cumene hydroperoxide is obtained in a selectivity of 99.9% at a cumene conversion of 30.8%.

EXAMPLE 1b (ACCORDING TO THE INVENTION)

The reaction product mixture from the oxidation (Example 1a) is concentrated on a rotary evaporator by evaporation of unreacted cumene. The remaining liquid contains 70% by weight of cumene hydroperoxide. The concentrate is taken up in 10 ml of acetone and added at 50° C. to a mixture of 90 ml of acetone and a small amount of sulphuric acid (1500 ppm). After 15 minutes, the composition of the reaction mixture is determined by means of GC. At a quantitative conversion of cumene hydroperoxide, phenol is obtained with a selectivity of 92% and acetone is obtained with a selectivity of 91%.

EXAMPLE 2 (NOT ACCORDING TO THE INVENTION, USING COCATALYST)

In a round-bottom flask fitted with superposed reflux condenser, 30 mmol of cumene are admixed at a temperature of 125° C. with 0.3 mmol of N-hydroxyphthalimide and 0.3 mmol of cobalt(II) acetate. The reaction mixture is stirred at the specified temperature under an oxygen atmosphere of 1 bar for 8 hours. The target product is not formed, but instead acetophenone with a selectivity of 58.7%, 2-phenyl-2-propanol (13.1%) and phenol (10.4%) are obtained at a cumene conversion of 49.3%.

EXAMPLE 3a (ACCORDING TO THE INVENTION)

In a round-bottom flask fitted with superposed reflux condenser, 30 mmol of cyclohexylbenzene are admixed at a temperature of 110° C. with 0.3 mmol of N-hydroxyphthalimide and 0.6 mmol of 1-cyclohexylbenzene hydroperoxide. The reaction mixture is stirred at the specified temperature under an oxygen atmosphere of 1 bar for 8 hours. 1-Cyclohexylbenzene hydroperoxide is obtained in a selectivity of 96.2% at a cyclohexylbenzene conversion of 28.6%.

EXAMPLE 3b (ACCORDING TO THE INVENTION)

The reaction product mixture from the oxidation (Example 3a) is concentrated on a rotary evaporator by evaporation of unreacted cyclohexylbenzene. The remaining liquid contains 65% by weight of 1-cyclohexylbenzene hydroperoxide.

The concentrate is taken up in 10 ml of acetone and added at 50° C. to a mixture of 90 ml of acetone and a small amount of sulphuric acid (1500 ppm). After 30 minutes, the composition of the reaction mixture is determined by means of GC. At a quantitative conversion of 1-cyclohexylbenzene hydroperoxide, phenol is obtained with a selectivity of 88% and cyclohexanone is obtained with a selectivity of 91%.

EXAMPLE 4a (NOT ACCORDING TO THE INVENTION, USING COCATALYST)

In a round-bottom flask fitted with superposed reflux condenser, 30 mmol of cyclohexylbenzene are admixed at a temperature of 110° C. with 0.3 mmol of N-hydroxyphthalimide and 0.3 mmol of cobalt(II) acetate. The reaction mixture is stirred at the specified temperature under an oxygen atmosphere of 1 bar for 8 hours. 1-cyclohexylbenzene hydroperoxide is obtained with a selectivity of 54.1% at a cyclohexylbenzene conversion of 18.7%.

EXAMPLE 4b (NOT ACCORDING TO THE INVENTION)

The reaction product mixture from the oxidation (Example 4a) is concentrated on a rotary evaporator by evaporation of unreacted cyclohexylbenzene. The remaining liquid contains 35% by weight of 1-cyclohexylbenzene hydroperoxide.

The concentrate is taken up in 10 ml of acetone and added at 50° C. to a mixture of 90 ml of acetone and a small amount of sulphuric acid (1500 ppm). After 30 minutes, the composition of the reaction mixture is determined by means of GC. At a quantitative conversion of 1-cyclohexylbenzene hydroperoxide, phenol is obtained with a selectivity of 30% and cyclohexanone is obtained with a selectivity of 32%.

EXAMPLE 5a (ACCORDING TO THE INVENTION)

In a round-bottom flask fitted with superposed reflux condenser, 30 mmol of cyclododecylbenzene are admixed at a temperature of 125° C. with 0.3 mmol of N-hydroxyphthalimide and 0.6 mmol of cyclododecylbenzene hydroperoxide. The reaction mixture is stirred at the specified temperature under an oxygen atmosphere of 1 bar for 8 hours. Cyclododecylbenzene hydroperoxide is obtained in a selectivity of 95.1% at a cyclododecylbenzene conversion of 23.1%.

EXAMPLE 5b (ACCORDING TO THE INVENTION)

The reaction product mixture from the oxidation (Example 5a) is concentrated on a rotary evaporator by evaporation of unreacted cyclododecylbenzene. The remaining liquid contains 60% by weight of cyclododecylbenzene hydroperoxide.

The concentrate is taken up in 10 ml of acetone and added at 50° C. to a mixture of 90 ml of acetone and a small amount of sulphuric acid (1500 ppm). After 35 minutes, the composition of the reaction mixture is determined by means of GC. At a quantitative conversion of cyclododecylbenzene hydroperoxide, phenol is obtained with a selectivity of 87% and cyclododecanone is obtained with a selectivity of 90%.

EXAMPLE 6a (NOT ACCORDING TO THE INVENTION, USING COCATALYST)

In a round-bottom flask fitted with superposed reflux condenser, 30 mmol of cyclododecylbenzene are admixed at a temperature of 125° C. with 0.3 mmol of N-hydroxyphthalimide and 0.3 mmol of cobalt(II) acetate. The reaction mixture is stirred at the specified temperature under an oxygen atmosphere of 1 bar for 8 hours. Cyclododecylbenzene hydroperoxide is obtained with a selectivity of 59.1% at a cyclododecylbenzene conversion of 7.3%.

EXAMPLE 6b (NOT ACCORDING TO THE INVENTION)

The reaction product mixture from the oxidation (Example 6a) is concentrated on a rotary evaporator by evaporation of unreacted cyclododecylbenzene. The remaining liquid contains 33% by weight of cyclododecylbenzene hydroperoxide.

The concentrate is taken up in 10 ml of acetone and added at 50° C. to a mixture of 90 ml of acetone and a small amount of sulphuric acid (1500 ppm). After 35 minutes, the composition of the reaction mixture is determined by means of GC. At a quantitative conversion of cyclododecylbenzene hydroperoxide, phenol is obtained with a selectivity of 28% and cyclododecanone is obtained with a selectivity of 32%.

What is claimed is:

1. A process comprising catalytically oxidizing an aromatic hydrocarbon to form a hydroperoxide, and subsequently cleaving the hydroperoxide to form a phenol derivative and a ketone, wherein the aromatic hydrocarbon is a compound of the formula IV

where $R^1$, $R^2$=aliphatic hydrocarbon radical having from 1 to 20 carbon atoms, where $R^1$ and $R^2$ are identical or different and $R^1$ and $R^2$ are joined to one another via a covalent bond, and Ar=aromatic hydrocarbon radical, wherein the process is carried out in the presence of an oxidization catalyst of the formula I and a free-radical initiator, wherein the molar ratio of the catalyst to the aromatic hydrocarbon is less than 10 mol %,

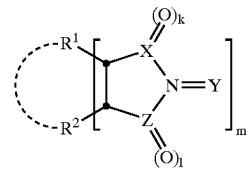

where $R^1$, $R^2$ is a group selected from the group consisting of H, aliphatic alkoxy radical, aromatic alkoxy radical, carboxyl radical, alkoxycarbonyl radical and hydrocarbon radical, in each case having one or more groups selected from the group consisting of from 1 to 20 carbon atoms, $SO_3H$, $NH_2$, OH, F, Cl, Br, I and $NO_2$, where $R^1$ $R^2$ are identical or different radicals or $R^1$ and $R^2$ may be joined to one another via a covalent bond, and X, Z=C, S, $CH_2$,
O, OH,
k=0, 1, 2,
l=0, 1, 2, and
m=1–3,
wherein when X=C, k must be 1; when Z=C, l must be 1; when X=S, k must be 2; when Z=S, k must be 2; when X=$CH_2$, k must be 0; when Z=$CH_2$, l must be 0.

2. The process according to claim 1, wherein the molar ratio of the oxidation catalyst to the aromatic hydrocarbon is from $10^{-6}$ mol % to 10 mol %.

3. The process according to claim 2, wherein the molar ratio of the oxidation catalyst to the aromatic hydrocarbon is from $10^{-6}$ mol % to 2.5 mol %.

4. The process according to claim 1, wherein the free-radical initiator is a peroxy compound or an azo compound.

5. The process according to claim 4, wherein the free-radical initiator and the oxidation catalyst are present in a molar ratio of 4:1.

6. The process according to claim 1, wherein the catalytic oxidation is carried out in the liquid phase at a temperature of from 0 to 500° C.

7. The process according to claim 1, wherein an oxidant is a gas comprising from 5 to 100% by volume of oxygen.

8. The process according to claim 1, wherein the catalytic oxidation is carried out under a pressure of from 1 to 100 bar.

9. The process according to claim 1, wherein the aromatic hydrocarbon is a compound of the formula VI or VII

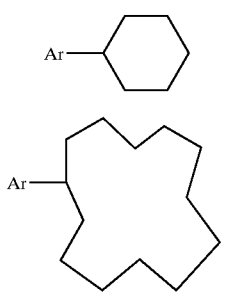

where Ar=aromatic hydrocarbon radical.

10. A process comprising catalytically oxidizing an aromatic hydrocarbon to form a hydroperoxide, and subsequently cleaving the hydroperoxide to form a phenol derivative and a ketone, wherein the aromatic hydrocarbon is a compound of the formula IV

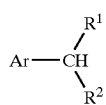

where $R^1$, $R^2$, =aliphatic hydrocarbon radical having from 1 to 20 carbon atoms, where $R^1$ $R^2$ are identical or different and $R^1$ and $R^2$ are joined to one another via a covalent bond, and Ar=aromatic hydrocarbon radical, wherein the process is carried out in the presence of an oxidization catalyst of the formula III and a free-radical initiator, wherein the molar ratio of the catalyst to the aromatic hydrocarbon is less than 10 mol %,

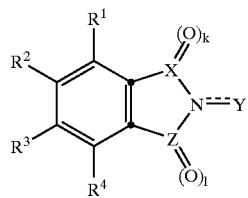

where $R^1$, $R^2$, $R^3$, $R^4$ is a group selected from the group consisting of H, aliphatic alkoxy radical, aromatic alkoxy radical, carboxyl radical, alkoxycarbonyl radical and hydrocarbon radical, in each case having one or more groups selected from the group consisting of from 1 to 20 carbon atoms, $SO_3H$, $NH_2$, OH, F, Cl, Br, I and $NO_2$, where $R^1$, $R^2$, $R^3$, $R^4$ are identical or different, and

X, Z=C, S, $CH_2$,

Y=O, OH, k=0, 1, 2, and l=0,1,2, wherein when X=C, k must be 1; when Z=C, l must be 1; when X=S, k must be 2; when Z=S, k must 2; when X=$CH_2$, k must be 0; when Z=$CH_2$, l must be 0.

11. The process according to claim 10, wherein the molar ratio of the oxidation catalyst to the aromatic hydrocarbon is from $10^{-6}$ mol % to 10 mol %.

12. The process according to claim 11, wherein the molar ratio of the oxidation catalyst to the aromatic hydrocarbon is from $10^{-6}$ mol % to 2.5 mol %.

13. The process according to claim 10, wherein the free-radical initiator is a peroxy compound or an azo compound.

14. The process according to claim 13, wherein the free-radical initiator and the oxidation catalyst are present in a molar ratio of 4:1.

15. The process according to claim 10, wherein the catalytic oxidation is carried out in the liquid phase at a temperature of from 0 to 500° C.

16. The process according to claim 10, wherein an oxidant is a gas comprising from 5 to 100% by volume of oxygen.

17. The process according to claim 10, wherein the catalytic oxidation is carried out under a pressure of from 1 to 100 bar.

18. The process according to claim 10, wherein the aromatic hydrocarbon is a compound of the formula VI or VII.

* * * * *